US012653934B2

(12) United States Patent
Biermann

(10) Patent No.: US 12,653,934 B2
(45) Date of Patent: Jun. 16, 2026

(54) APPARATUS FOR EXTRACORPOREAL BLOOD TREATMENT

(71) Applicant: FRESENIUS MEDICAL CARE DEUTSCHLAND GMBH, Bad Homburg (DE)

(72) Inventor: Frank Biermann, Hamburg (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 296 days.

(21) Appl. No.: 18/275,611

(22) PCT Filed: Feb. 8, 2022

(86) PCT No.: PCT/EP2022/052953
§ 371 (c)(1),
(2) Date: Aug. 3, 2023

(87) PCT Pub. No.: WO2022/171596
PCT Pub. Date: Aug. 18, 2022

(65) Prior Publication Data
US 2024/0115779 A1 Apr. 11, 2024

(30) Foreign Application Priority Data
Feb. 9, 2021 (DE) ..................... 10 2021 102 993.7

(51) Int. Cl.
*A61M 1/14* (2006.01)
*A61B 5/0215* (2006.01)
(Continued)

(52) U.S. Cl.
CPC .......... *A61M 1/154* (2022.05); *A61B 5/0215* (2013.01); *A61M 1/36224* (2022.05); *G01L 7/00* (2013.01);
(Continued)

(58) Field of Classification Search
CPC .............. A61M 1/154; A61M 1/36224; A61M 2205/3331; G01L 7/00; G01L 19/0007; G01L 19/04; G01L 19/06; A61B 5/0215
(Continued)

(56) References Cited

U.S. PATENT DOCUMENTS

| 10,564,060 B2 * | 2/2020 | Schofield .............. F01D 21/003 |
| 2009/0230036 A1 * | 9/2009 | Apel ................... A61M 1/3644 |
| | | 210/120 |

(Continued)

FOREIGN PATENT DOCUMENTS

| DE | 102005022545 A1 * | 11/2006 | .......... A61M 1/3644 |
| DE | 102009001901 A1 * | 9/2010 | .......... A61M 1/3639 |

(Continued)

OTHER PUBLICATIONS

International Search Report and Written Opinion (with English translation of International Search Report) issued in corresponding International Patent Application No. PCT/EP2022/052953 mailed May 9, 2022 (13 pages).

*Primary Examiner* — Stephanie E Bloss
*Assistant Examiner* — Kevin C Butler
(74) *Attorney, Agent, or Firm* — Kilyk & Bowersox, P.L.L.C.

(57) ABSTRACT

A pressure-measuring device according to the invention has a hydrophobic membrane, which is air permeable in the dry state and air impermeable in a moistened state, and a pressure sensor, which is in mechanical contact with the hydrophobic membrane and which is designed to follow a movement of the membrane. During the filling of a line system, air is separated via the hydrophobic membrane and, in the air-impermeable state, the pressure in the line system is measured by means of the moistened hydrophobic membrane.

15 Claims, 7 Drawing Sheets

(51) Int. Cl.
*A61M 1/36* (2006.01)
*G01L 7/00* (2006.01)
*G01L 19/00* (2006.01)
*G01L 19/04* (2006.01)
*G01L 19/06* (2006.01)

(52) U.S. Cl.
CPC .......... *G01L 19/0007* (2013.01); *G01L 19/04* (2013.01); *G01L 19/06* (2013.01); *A61M 2205/3331* (2013.01)

(58) Field of Classification Search
USPC .......................................................... 73/700
See application file for complete search history.

(56) References Cited

U.S. PATENT DOCUMENTS

| | | | | |
|---|---|---|---|---|
| 2012/0095351 | A1 * | 4/2012 | Klose ................. | A61M 1/3641 |
| | | | | 600/483 |
| 2012/0261316 | A1 * | 10/2012 | Kreber ............... | A61M 1/1694 |
| | | | | 210/97 |
| 2014/0076058 | A1 * | 3/2014 | Brugger ............... | G01L 9/0041 |
| | | | | 73/723 |
| 2019/0250058 | A1 * | 8/2019 | Schofield ............... | F01D 17/08 |
| 2021/0138131 | A1 * | 5/2021 | Fini ....................... | A61M 1/267 |
| 2024/0115779 | A1 * | 4/2024 | Biermann .......... | G01L 19/0654 |

FOREIGN PATENT DOCUMENTS

| | | | | | |
|---|---|---|---|---|---|
| DE | 102011016870 | A1 | * | 10/2012 | ......... A61M 1/1694 |
| DE | 102021102993 | A1 | * | 8/2022 | ........ G01L 19/0654 |
| EP | 1319417 | A1 | * | 6/2003 | ......... A61M 1/3639 |
| EP | 1595560 | A1 | * | 11/2005 | ......... A61M 1/3465 |
| EP | 2583702 | A1 | * | 4/2013 | ........... A61M 1/365 |
| EP | 2662101 | A1 | * | 11/2013 | ......... A61M 1/3643 |
| JP | 2009297340 | A | * | 12/2009 | |
| JP | 6637108 | B2 | * | 1/2020 | ............. A61M 1/36 |
| WO | WO-2012126744 | A1 | * | 9/2012 | ........ A61M 5/16809 |
| WO | WO-2012166980 | A2 | * | 12/2012 | ........ G01L 19/0046 |
| WO | WO-2019221204 | A1 | * | 11/2019 | ............. A61M 1/36 |
| WO | WO-2021119401 | A1 | * | 6/2021 | ......... A61M 39/223 |

* cited by examiner

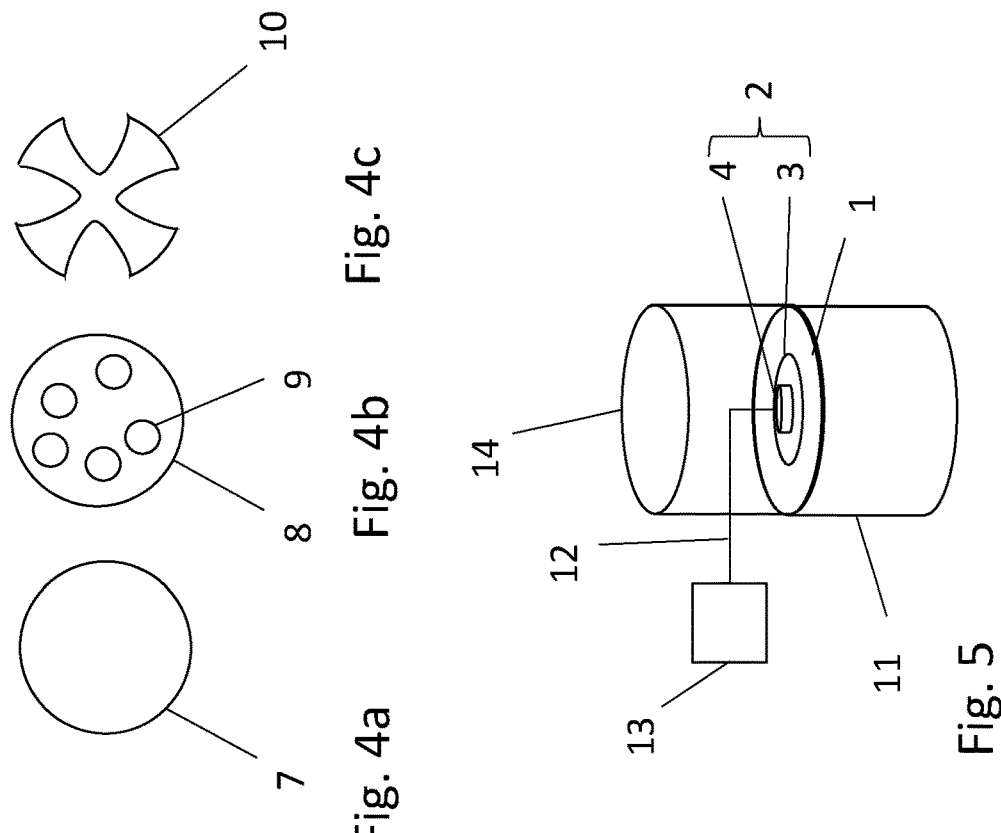
Fig. 4a
Fig. 4b
Fig. 4c
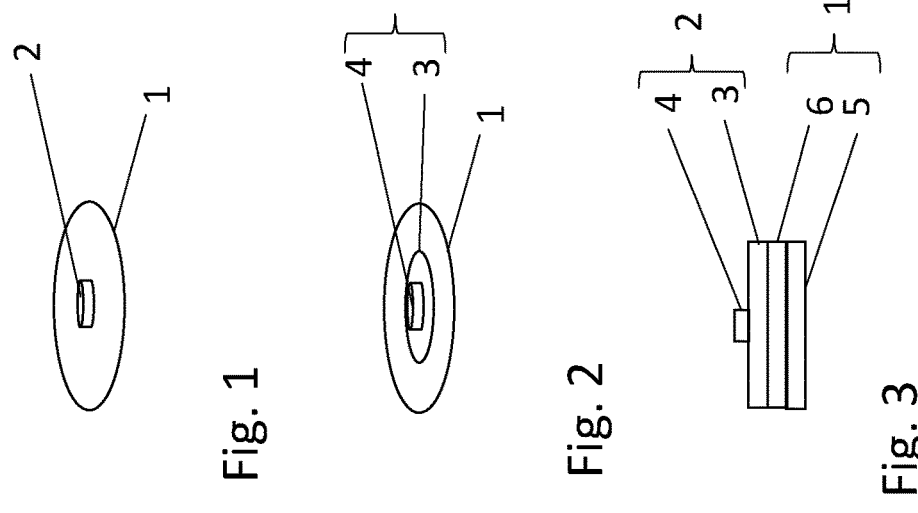
Fig. 5
Fig. 1
Fig. 2
Fig. 3

1

APPARATUS FOR EXTRACORPOREAL BLOOD TREATMENT

This application is a National Stage Application of PCT/EP2022/052953, filed Feb. 8, 2022, which claims priority to German Patent Application No. 10 2021 102 993.7, filed Feb. 9, 2021.

FIELD OF THE INVENTION

The invention relates to a pressure-measuring device and to a medical functional device which is connectable to the pressure-measuring device. The invention further relates to a method for filling the medical functional device, wherein the pressure-measuring device can be used to measure the pressure in the filled medical functional device.

BACKGROUND

Pressure measurements in liquid-conveying lines are necessary, for example, in dialysis technology, for example in order to monitor the correct function of the dialysis appliances.

In hemodialysis, in which blood is cleaned outside the body by means of a dialysis appliance, as an example of an extracorporeal blood treatment device, one or more pressure-measuring devices can therefore be provided at various locations of the blood-conveying system. These locations are for example:

between a patient-side end of an arterial line and a pump, which can be arranged along this arterial line (arterial pressure-measuring device), between the pump and a dialyzer (prefilter pressure-measuring device), on a venous line, by means of which the blood is returned from the dialyzer to the patient, between the dialyzer and an air separation chamber (postfilter pressure-measuring device).

As pressure-measuring devices, various pressure sensors are known. For example, pressure sensors are used in which the pressure is detected via an air-impermeable and liquid-impermeable membrane, on the basis of the deflection of the membrane. Other pressure sensors provide an air cushion which is positioned in such a way that the air in the air cushion is compressed, when there is a higher pressure in the liquid-conveying line, and the pressure can be measured by means of a pressure sensor connected to this air cushion. A disadvantage of this last solution is in particular that a blood-air interface arises here during the treatment. Such pressure-measuring units with an air cushion often have a pressure-transmitting element for protecting the machine-side air lines. This pressure-transmitting element has a hydrophobic membrane which is air permeable in the dry state and is impermeable to liquid. In order for the pressure-measuring unit to function, this hydrophobic membrane must not be moistened, since the air cannot then pass through the membrane, when there is a change of the pressure in the liquid-conveying line, and the air in the air cushion can therefore no longer be compressed.

However, to be able to measure the pressure in a liquid-conveying line, the line first of all has to be filled. In other words, the air in the line has to be replaced by the liquid. This procedure is called priming or filling in dialysis, wherein in this step the patient is not yet connected to the dialysis appliance, in particular not to the arterial or venous line. It is therefore important that the air is removed from the lines as completely as possible, because otherwise air could enter the patient's vein.

There are many solutions in respect of this filling procedure. For example, the air can be separated via a pressure-measuring unit with an air cushion, as described above, which additionally has an opening to the outside. In other words, during the priming/filling, the air is moved via the hydrophobic membrane in the direction of the air pressure sensor and conveyed to the outside. During this procedure, the pressure-measuring system is open to the outside.

The object of the invention is to make available a new type of pressure-measuring device that satisfies the various functions of conventional pressure-measuring devices, but without the disadvantages of the latter.

DESCRIPTION OF THE INVENTION

A pressure-measuring device has a hydrophobic membrane, which is air permeable in the dry state and air impermeable in a moistened state, and a pressure sensor, which is in mechanical contact with the hydrophobic membrane and which is designed to follow a movement of the membrane.

The pressure-measuring can moreover have a first chamber, which is arranged on a front side of the hydrophobic membrane, and a second chamber, which is arranged on a rear side of the hydrophobic membrane. The pressure sensor in the second chamber can be arranged on the hydrophobic membrane.

The pressure sensor of the pressure-measuring device can have a pressure-measuring sensor system, in particular a strain gauge sensor system or a piezoelectric sensor. The pressure sensor can moreover have a carrier layer on which the pressure-measuring sensor system is arranged. The pressure-measuring sensor system can be arranged on the side of the carrier layer directed away from the hydrophobic membrane.

The carrier layer can have an elastic membrane. The edge region of the carrier layer can be secured with pretensioning on the first chamber or the second chamber. The carrier layer can be secured on the hydrophobic membrane.

The first chamber of the pressure-measuring device, together with the hydrophobic membrane, can be secured releasably on the second chamber.

The first chamber of the pressure-measuring device, together with the hydrophobic membrane and the pressure sensor, can be secured releasably on the second chamber.

The pressure sensor of the pressure-measuring device can moreover have a cable line in order to transmit an electrical signal to an evaluation unit, wherein the cable line can optionally have a connector unit for connecting and/or releasing the pressure sensor with respect to the evaluation unit.

The first chamber of the pressure-measuring device can have at least two channels, which are each closed off at one end by the hydrophobic membrane. The at least two channels can be shut off individually.

A medical functional device can have at least one blood line and/or a dialyzer, for use with the pressure-measuring device, wherein the first chamber and the hydrophobic membrane are part of the medical functional device. Alternatively, the first chamber and the hydrophobic membrane and the pressure sensor can be part of the medical functional device.

The medical functional device can have a line section which is designed for insertion into a peristaltic pump. The medical functional device can have an impeller for use in an impeller pump. The medical functional device can have a chamber with a membrane for use in a diaphragm pump. The pressure-measuring device can be arranged fluidically upstream or downstream from the pump.

The medical functional device can have an air separation chamber, wherein the pressure-measuring device can be arranged fluidically upstream or downstream from the air separation chamber. The medical functional device can have a dialyzer, wherein the pressure-measuring device can be arranged on the dialyzer.

A method for measuring a pressure using the pressure-measuring device can comprise the following steps:

filling the blood hose system with a liquid by displacement of air in the blood hose system through the hydrophobic membrane, wherein the hydrophobic membrane is wetted by the liquid such that it becomes impermeable to air or becomes impermeable to air in the region of one of the at least two channels, and measuring the change of the position of the membrane, in particular of its shape, by the pressure sensor.

The term "pressure-measuring device", within the meaning of this description, signifies that it includes at least essential elements according to the invention for the measurement of pressure. The term is not to be understood as meaning that all of the elements that are technically necessary, for example also for evaluating a pressure measurement, have to be encompassed by said term. For example, the pressure sensor can be provided to measure an altered curvature of the membrane, and an evaluation unit, which converts this curvature into a pressure value, can be integrated in the pressure sensor itself, although it can also be made available as a separate unit. In this case, the evaluation unit does not necessarily have to be part of the pressure-measuring device.

In the figures:

FIG. 1 shows a schematic view of a structure of a pressure-measuring device;

FIG. 2 shows a schematic view of an embodiment of the structure of a pressure sensor;

FIG. 3 shows a schematic view of a layer structure of the pressure-measuring device;

Figures 6, 7:
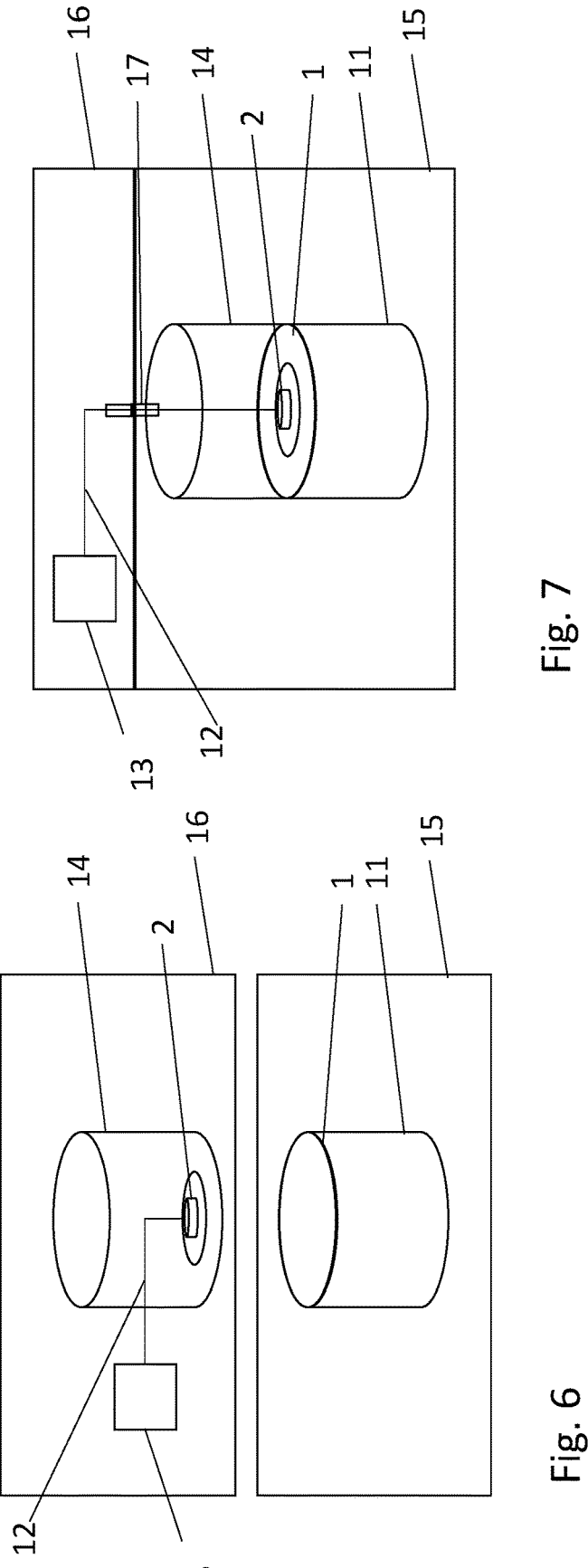
Figures 8A, 8B:
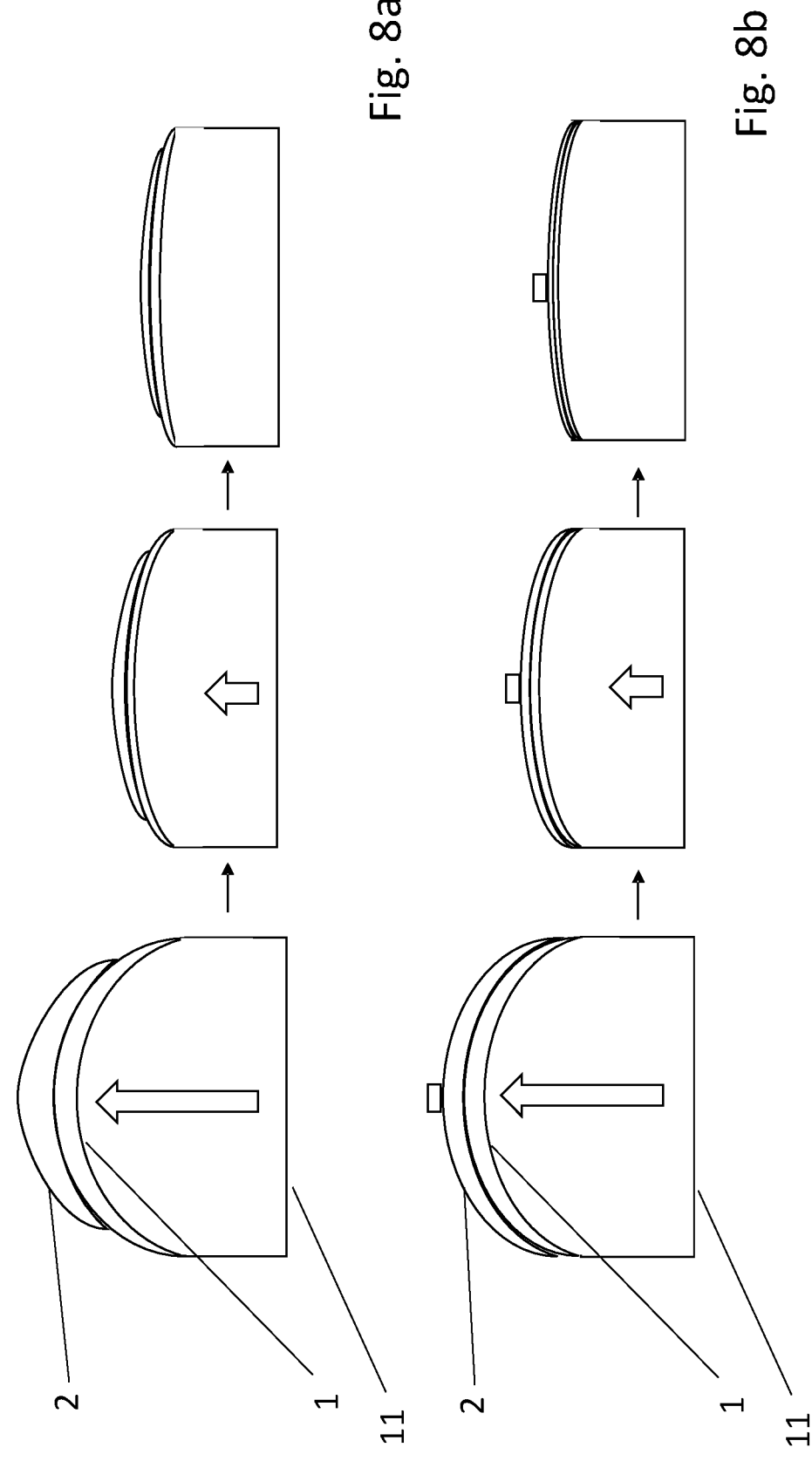
Figure 9:
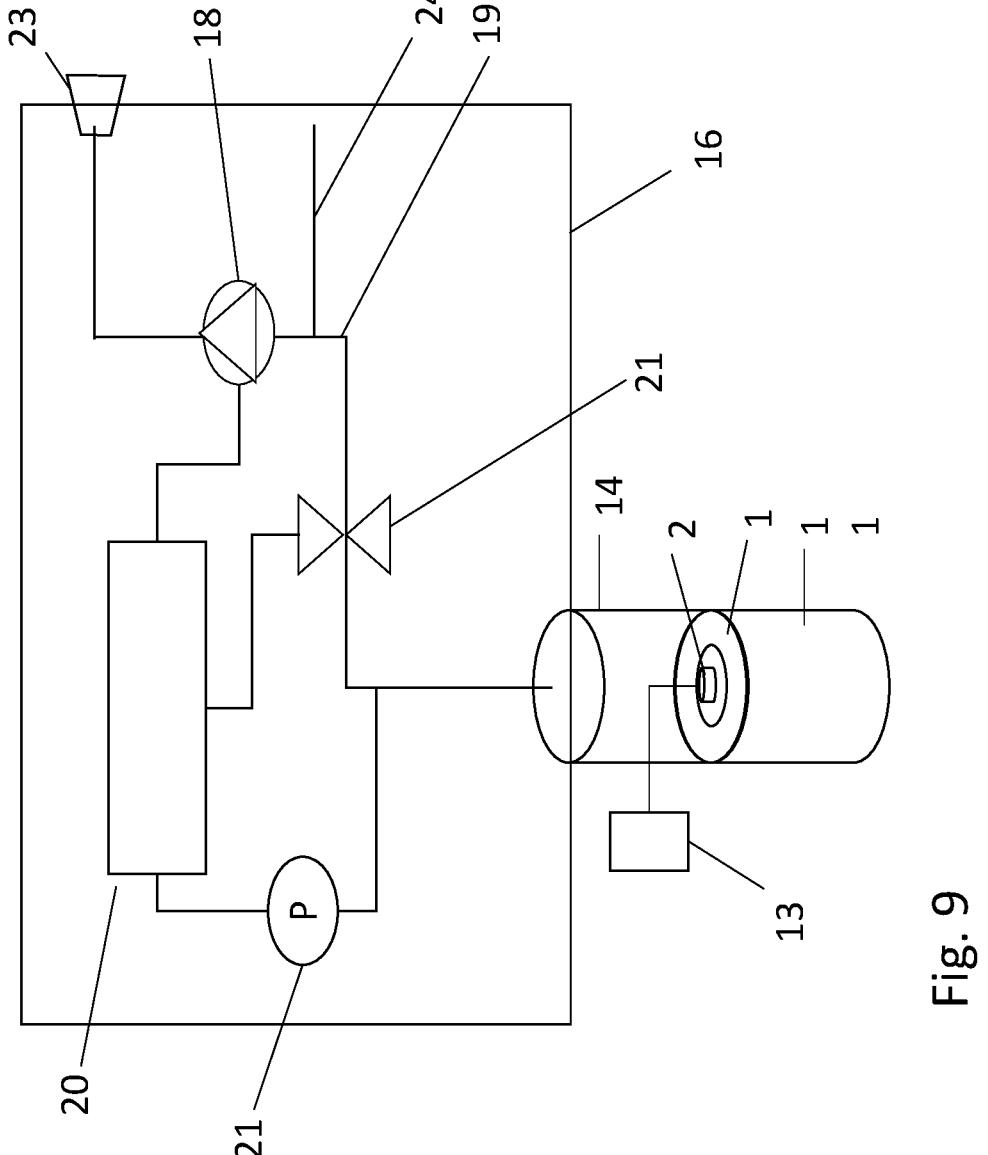
Figure 10:
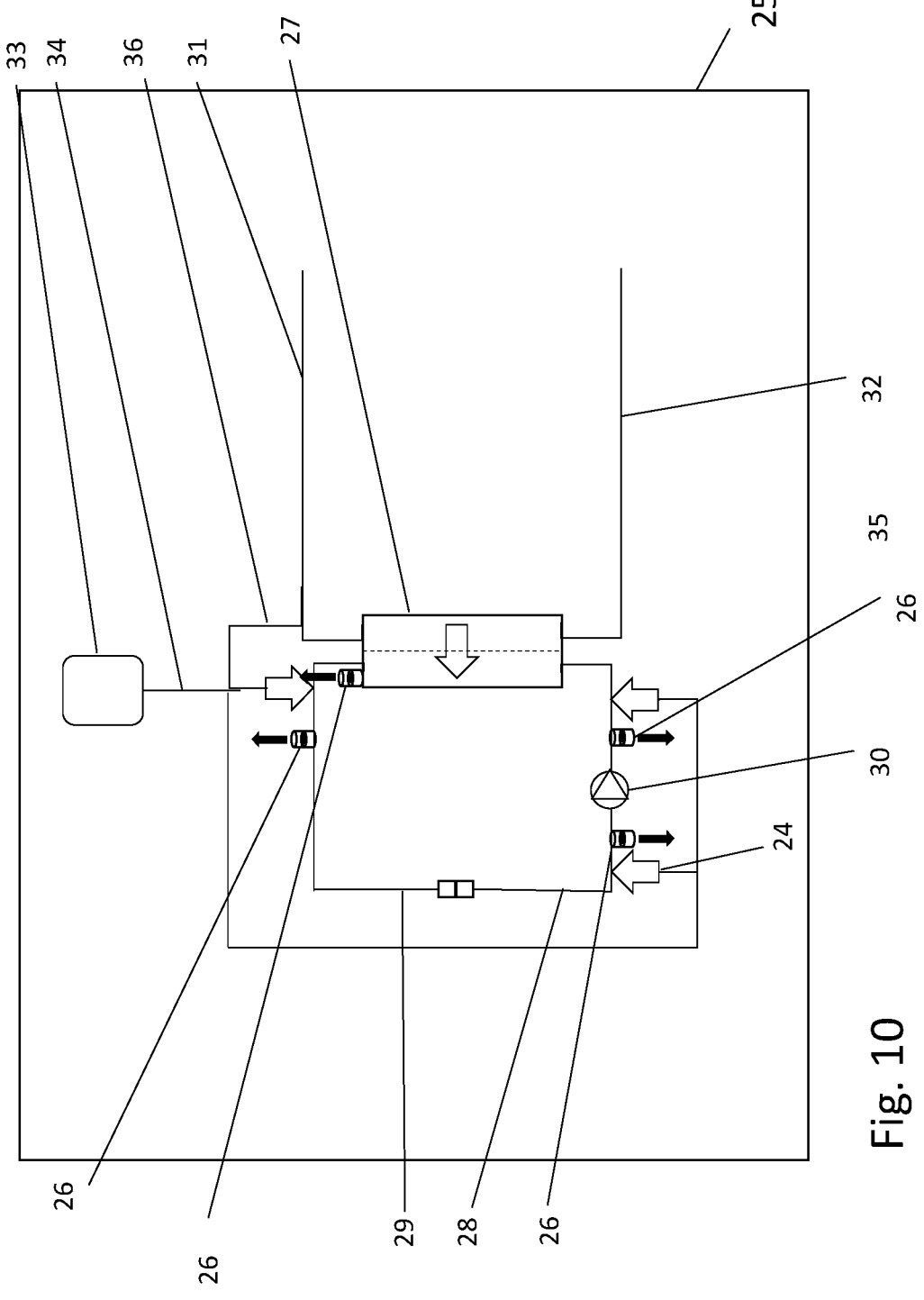
Figure 11:
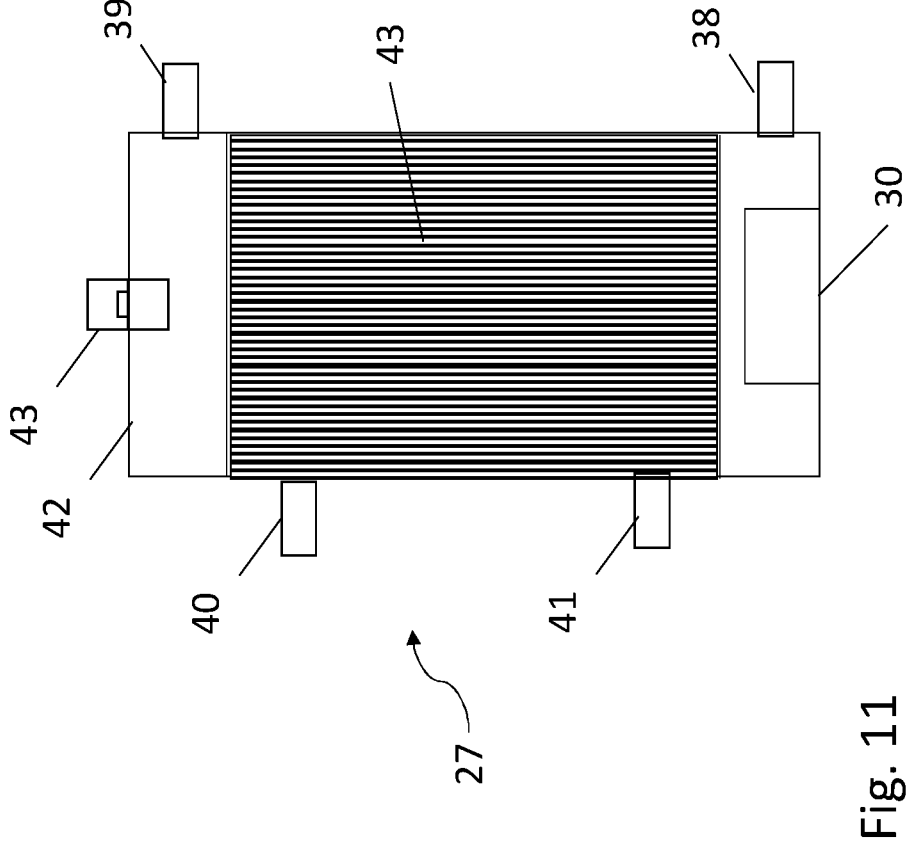
Figures 12, 13, 14, 15, 16:
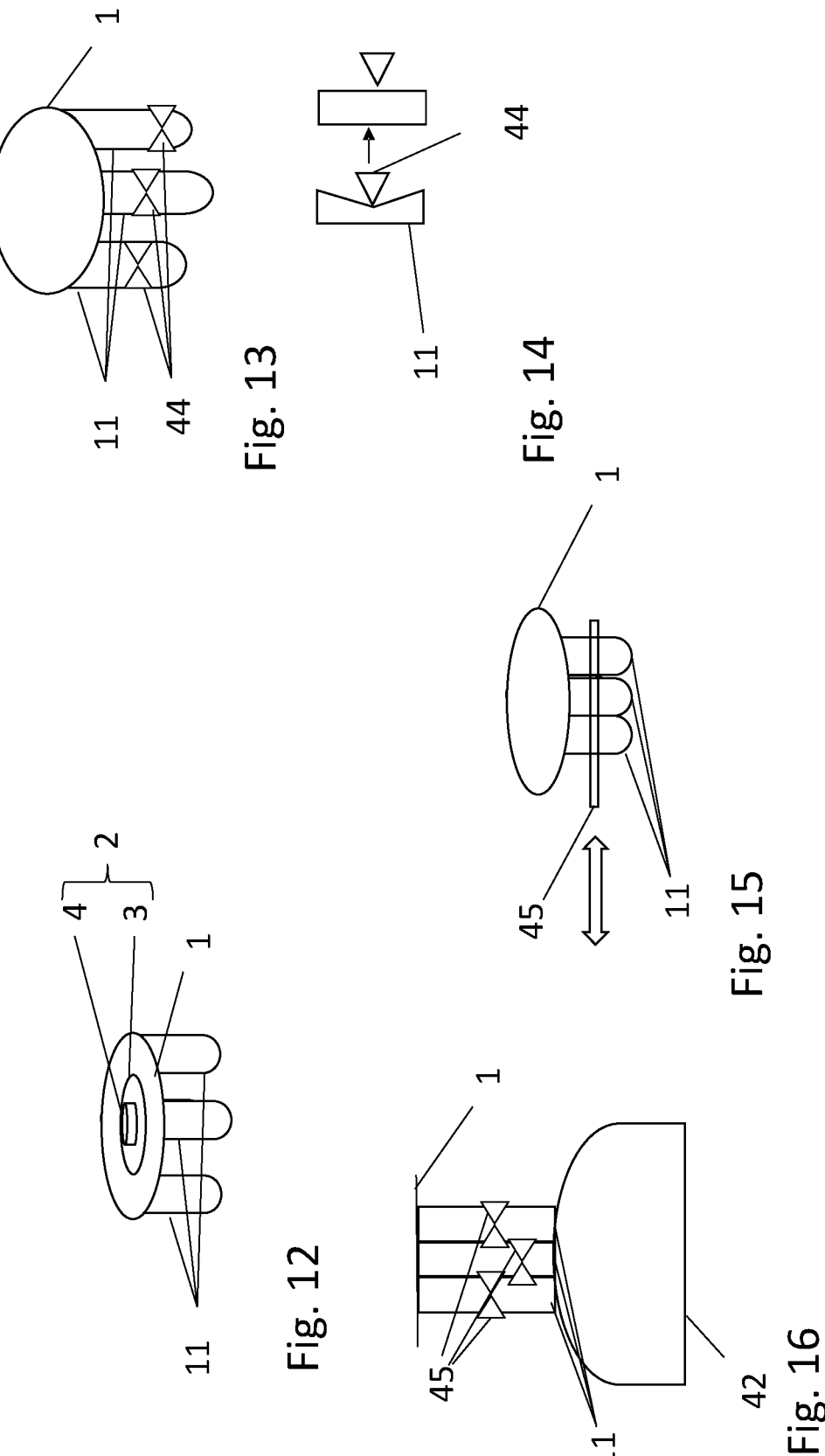

FIGS. 4*a* to 4*c* show schematic views of embodiments of a carrier layer;

FIG. 5 shows a schematic view of a structure of a pressure-measuring device with a first chamber and a second chamber;

FIGS. 6 and 7 show schematic views of how the pressure-measuring device can be integrated in a disposable and a treatment device;

FIGS. 8*a* and 8*b* show schematic views of embodiments of the mechanical coupling of a pressure sensor to a hydrophobic membrane;

FIG. 9 shows a schematic view of an embodiment of the coupling of a pressure sensor to a hydrophobic membrane using a negative pressure;

FIG. 10 shows a schematic view of an embodiment of a treatment system with a pressure-measuring device;

FIG. 11 shows a schematic view of an embodiment of a pressure-measuring device, in which the pressure-measuring device is integrated in a cap of a dialyzer;

FIG. 12 shows a schematic view of an embodiment of a pressure-measuring device with a plurality of channels as first chamber;

FIG. 13 shows a schematic view of an embodiment of an aeration device;

FIG. 14 shows a schematic view of an embodiment of the channels in the form of flexible elements and of the closure means of an aeration device;

FIG. 15 shows a schematic view of an embodiment of the channels and of the closure means in the form of a slide of an aeration device; and FIG. 16 shows a schematic view of the integration of an aeration device into a cap of a dialyzer.

In the description of the embodiments with reference to the figures, identical or comparable features are identified by the same reference signs. Such identical or comparable features are not described anew for each figure, and reference should therefore be made to the particular passages of the description in which these features have already been described.

FIG. 1 shows a schematic structure of a pressure-measuring device. The pressure-measuring device has a hydrophobic membrane 1 and a pressure sensor 2. The hydrophobic membrane 1 is air permeable in the dry state and air impermeable in a moistened state. The hydrophobic membrane 1 is also impermeable to water-based liquids. These liquids can comprise water, priming liquid (filling liquid), dialysate or blood. The pressure sensor 2 is in mechanical contact with the hydrophobic membrane 1. Through this mechanical contact, the pressure sensor 2 can detect a movement of the membrane 1. This is, for example, a movement of a hydrophobic membrane 1 secured at the edge, which leads to a curvature of the hydrophobic membrane 1. The movement can also be a translational movement of the hydrophobic membrane 1. The movement of the hydrophobic membrane 1 can be produced, for example, by a change of pressure on the side (front side) of the hydrophobic membrane 1 directed away from the sensor.

As is shown schematically in FIG. 2, the pressure sensor 2 can have a carrier layer 3. The pressure-measuring sensor system 4 of the pressure sensor 2 can be arranged on the carrier layer 3. The carrier layer 3 can be arranged between the pressure-measuring sensor system 4 and the hydrophobic membrane 1. In other words, the pressure-measuring sensor system 4 can be arranged on the side (rear side) of the carrier layer 3 directed away from the hydrophobic membrane. The movement of the hydrophobic membrane 1 can be able to be transmitted to the pressure-measuring sensor system 4 via the carrier layer 3. The pressure-measuring sensor system 4 of the pressure sensor 2 can have a strain gauge sensor system or a piezoelectric sensor.

The expression pressure-measuring device describes a device with which a pressure can be determined. The pressure-measuring device can have a pressure sensor. The expression pressure sensor describes a device which reacts to a change of the pressure. The pressure sensor can have a carrier layer and a pressure-measuring sensor system, wherein the expression pressure-measuring sensor system describes a device which, in the event of the pressure changing, experiences a change and can thereby generate a signal.

The carrier layer 3 can be connected fixedly or releasably to the pressure-measuring sensor system 4.

The carrier layer 3 can be connected fixedly or releasably to the hydrophobic membrane 1.

As is shown schematically in FIG. 3, the hydrophobic membrane 1 can have or consist of at least one layer 5 of a hydrophobic material. The hydrophobic material can have or consist of a hydrophobic plastic. For example, the hydrophobic plastic can be or have PTFE (polytetrafluoroethylene) or ePTFE (expanded polytetra-fluoroethylene).

The hydrophobic membrane 1 can consist of or have two or more layers, for example a first layer 5 made of or having the hydrophobic material, and a second layer 6 which has a drainage and/or support function and is made of or has a woven and/or nonwoven that can be welded and/or adhesively bonded. Alternatively, in addition to the aforementioned layers, the hydrophobic membrane 1 can have further layers or constituents. The first layer 5 can be connected to the second layer 6 across the surface or only in the edge region along the circumference of the first layer 5 and of the second layer 6, for example welded or adhesively bonded.

The carrier layer 3 can also be the second layer 6 of the hydrophobic membrane 1, or the second layer 6 of the hydrophobic membrane 1 can be a layer which is present in addition to the carrier layer 3.

The carrier layer 3 can be a plastic layer. The carrier layer 3 can be or have a thin, flexible ceramic layer. The carrier layer 3 has a flexibility, such that it can transmit movements of the hydrophobic membrane 1.

In other words, the layer structure can be as follows:

On the front side a hydrophobic membrane layer 5, optionally arranged thereon a layer 6 with drainage and/or support function, optionally arranged thereon the carrier layer 3, and arranged thereon the pressure-measuring sensor system 4.

FIGS. 4a to 4c show schematic views of embodiments of the carrier layer 3. The carrier layer 3 can have a closed membrane 7. Here, the term "closed" signifies that the membrane has no macroscopic openings, and instead it has a material that is homogeneous across the surface. The closed membrane 7 can cover the whole surface of the hydrophobic membrane 1. Since, in this embodiment of the closed membrane 7, the air that passes through the hydrophobic membrane 1 also has to pass through the closed membrane 7, the closed membrane 7 is permeable to air. In a further embodiment, the closed membrane 7 can only partially cover the hydrophobic membrane. In such an embodiment, the closed membrane 7 can also be impermeable to air. The carrier layer 3 can also have or consist of an opened membrane 8. Here, the term "opened" signifies that the membrane has one or more macroscopic openings 9. The surface area of the openings 9 can be of the order of 1 to 1000 square millimeters or of the order of 1 to 10 square centimeters. In one embodiment, the opened membrane 8 can have a closed edge region or, in a further embodiment, the opening can also comprise the edge region, as is shown schematically in FIG. 4c, such that the opened membrane 8 is a webbed membrane 10.

As is shown schematically in FIG. 5, the pressure-measuring device can have a first chamber 11. A part of the wall of the first chamber 11 can be closed off by the hydrophobic membrane 1. The hydrophobic membrane, or the second layer 6 if present, can be connected at its outer edge to the first chamber 11 in a fluid-tight manner. The connection can be provided by adhesive bonding, welding and/or crimping. The first chamber 11 can be formed from a hard plastic, for example polypropylene or hard PCV, or the wall can have this material. The first chamber 11 can be a through-flow chamber. The through-flow chamber can have two or more openings in its wall. The first chamber 11 can be a dead-end chamber. The dead-end chamber can have precisely one opening. The first chamber 11 can be part of a disposable. The disposable can be a hose set, a cartridge or a dialyzer. The disposable can in particular be a fluid line system which is provided for a dialysis treatment, for example for hemodialysis, hemofiltration, hemodiafiltration, ultrafiltration or diaphragm dialysis or peritoneal dialysis. Here, the term disposable signifies that the disposable is placed on the treatment device by the user for the treatment of one patient, generally a new disposable for each treatment. Normally, for hygiene reasons, disposables should be used only once. However, cost aspects for example may lead to a situation where disposables are used more than once. It is important that a disposable is not a permanent constituent part of the treatment device, but only during the treatment forms a functional unit with the treatment device. For this purpose, reference is also made to the description of FIGS. 6 and 7.

The pressure-measuring sensor system 4 can be connected to a processor 13 via a signal line 12. The processor 13 can be programmed to process a signal transmitted by the pressure-measuring sensor system 4 and to determine a pressure value therefrom. The processor 13 can forward this pressure value to a further processor, wherein the further processor can be programmed, on the basis of the pressure value, to perform one or more method steps or cause these method steps to be performed. The processor 13 can be programmed to also carry out itself the functions of the further processor. The processor 13 can be part of a control device. The control device can have the processor 13 and optionally the further processor, a memory and a communication bus. The term processor is not limited here to an individual physical processor. Instead, the processor can also have a multicore processor or otherwise interconnected processors or processor constituents. The memory can be a volatile and/or non-volatile memory or a combination of these. The data bus can serve for the exchange of data between memory and processor. The control device can have the modular units of a computer that are known to a person skilled in the art and that are required in order to run a program and thereby control a medical device. In addition to the processors, memory and communication bus mentioned above, such modular units can also include interfaces to the devices that are to be controlled, such as actuators, sensors, displays, wired or wireless communications and the like.

As is shown schematically in FIG. 4, the pressure-measuring device can have a second chamber 14. The second chamber can be arranged on the rear side of the hydrophobic membrane 1. The second chamber 14 can be at least partially closed off by the hydrophobic membrane 1 and/or the second layer 6 and/or the carrier layer 3. The pressure-measuring sensor system can be arranged in the second chamber 14. The second camber 14 can be part of the treatment device or of the disposable. The second chamber 14 can be made of the same martial as the first chamber 11 or of another material. In particular, the second chamber 14, as part of the treatment device, can be made of or have metal.

FIGS. 6 and 7 show schematic views of how the pressure-measuring device can be integrated in a disposable 15 and a treatment device 16. The pressure-measuring device can be constructed in such a way that the hydrophobic membrane 1 is separable from the pressure sensor 2. The hydrophobic membrane 1 and optionally the first chamber 11 can be part of the disposable 15, and the pressure sensor 2 and optionally the second chamber 14 can be part of the treatment device 16. The treatment device 16 can have the signal line 12 and the processor 13. During use of the pressure-measuring device, the pressure sensor 2 and the hydrophobic membrane 1 are coupled mechanically to each other, such that a movement of the hydrophobic membrane 1 transmits to the pressure sensor 2. In an alternative embodiment, the hydrophobic membrane 1 and optionally the first chamber 11, the pressure sensor 2 and optionally the second chamber 14 are part of the disposable. The signal line 12 is separable and has a connector 17. The connector 17 has a first attachment at the side of the disposable and a second attachment at the side of the treatment device 16. The treatment device 16 can have at least one part of the signal line 12 and the processor 13. During use of the pressure-measuring device, the first attachment and the second attachment are connected to each other.

The coupling of the movement of the hydrophobic membrane 1 to the pressure sensor 2 can be effected in various ways. During this movement, the hydrophobic membrane 1 is not permeable to air, i.e. is in a wetted stated. In this way, a pressure compensation via the hydrophobic membrane can be prevented or blocked. This is described with reference to FIGS. 8a and 8b. Here, pressure signifies the differential pressure across the hydrophobic membrane 1.

The hydrophobic membrane 1 or the above-described second layer have an elasticity. By virtue of the elasticity, the hydrophobic membrane 1 or the above-described second layer follows the pressure. Here, elastic signifies that the hydrophobic membrane 1 or the above-described second layer is designed in such a way that a restoring force acts on the material such that, when no pressure is applied, it has a flatter configuration than when subjected to pressure. Here, the term "flat" or "flatter" signifies a lesser curvature. The hydrophobic membrane 1 or the above-described second layer can be pretensioned. Here, "pretensioned" signifies a securing of the hydrophobic membrane 1 or of the above-described second layer to a wall such that, upon release of the securing to the wall, the hydrophobic membrane 1 or the above-described second layer contracts.

The pressure sensor 2 can be connected directly to the hydrophobic membrane 1 or the above-described second layer, which is connected to the hydrophobic membrane 1. The hydrophobic membrane 1 and/or the second layer can be connected fixedly to a wall of the first chamber 11. If great pressure is now applied (indicated by the long arrow in FIGS. 8a and 8b), the hydrophobic membrane and, if present, the second layer are curved and thereby stretched. The pressure sensor 2 is thereby likewise stretched. When the pressure is reduced (shorter arrow) or set to zero (no arrow), the curvature decreases and, with it, the stretching of the second sensor.

A further embodiment, shown schematically in FIG. 8b, differs from the embodiment described in relation to FIG. 8a in that in this embodiment the pressure sensor 2 itself is secured to the wall of the first chamber 11 or of the second chamber. In particular, the securing can be a securing of the carrier layer of the pressure sensor 2. The pressure sensor 2 can be configured to be elastic and/or can be secured in a pretensioned state. To explain these features, reference is made to the explanation regarding the hydrophobic membrane 1. In this embodiment, it is possible for the pressure sensor 2 not to be connected to the hydrophobic membrane 1 and not to be connected to the above-described second layer. In this case, the hydrophobic membrane 1 and the above-described second layer may have no pretensioning. When, in this embodiment, great pressure is applied, the air-impermeable or moistened hydrophobic membrane 1 is pressed against the pressure sensor 2, and the latter curves out and thus permits a pressure measurement. When the pressure is reduced, the pressure sensor 2 contracts and the curvature decreases until, at a pressure of 0, the pressure sensor 2 is relaxed completely in the direction of the curvature. This embodiment is only suitable for measuring positive pressures since, in the case of negative pressures, the hydrophobic membrane 1 is pulled farther counter to the arrow direction in FIG. 8 and, since there is no fixed coupling between the hydrophobic membrane 1 and the pressure sensor 2, the pressure sensor 2 does not follow the hydrophobic membrane 1. Such an embodiment can be used particularly effectively in a situation where only positive pressure values are intended to be measured. An advantage of this embodiment is that it involves a relatively simple and cost-effective structure and, in particular, it is possible to do without the coupling. It has been found that the coupling should otherwise be tested for example during a treatment, which entails a corresponding outlay in terms of equipment and/or processes and/or time. This embodiment can be realized for example in combination with the embodiment described with reference to FIG. 6. In this resulting embodiment, the pretensioned pressure sensor at the treatment side simply has to be brought into contact with the membrane once disposable having that hydrophobic membrane is installed, and the positive pressures can be measured.

FIG. 9 shows a schematic view of a further possibility for the coupling. In this embodiment, the coupling of the pressure sensor 2 to the hydrophobic membrane 1 is effected by means of a vacuum. With such a coupling, the pressure sensor can be mounted releasably on the hydrophobic membrane 1. In this case, the pressure sensor 2 is impermeable to air at least in one portion of its surface. For this purpose, the treatment device 16 has a pump 18 and an air line 19, which is connectable or connected to the second chamber 14. With the pump 18, air can be aspirated from the second chamber 14. Optionally, the treatment device 16 can have one or more or all of the following component parts: a control device 20, a valve 21 for shutting off the air line 19, and a second pressure-measuring device 22 for measuring the pressure in the second chamber 14. The control device can be connected to the pump 18, the valve 21 and the second pressure-measuring device via signal lines. The control device 20 can be programmed to obtain the pressure value in the chamber 14 and, if the pressure value of the chamber 14 is above a limit value, to start the pump 18 and thus aspirate air out of the second chamber 14. The processor 13, which can process the signal from the pressure sensor 2, can be integrated in the control device 20, such that the processor 13 is also programmed to process further program sections of the treatment device 16, or the processor 13 can be a processor independent of the control device 20 and merely communicate with the control device 20.

The pump 18 can be a pump separately provided for the aspiration of air. The pump 18 can also be a pump which is used to pump a liquid, in particular dialysate in a treatment device for extracorporeal blood treatment, to an outlet 23 of the treatment device. This can mean that no separate outlet has to be provided for the gas to be discharged. For this purpose, the air line 19 can lead into a liquid line 24, and the pump 18 can be arranged downstream from the lead-in point.

FIG. 10 shows schematic views of various embodiments of a treatment system 25. In this figure, the above-described pressure-measuring device is labeled with the reference number 26. The pressure-measuring device can be arranged once, twice, three times or four times or more than four times (not shown) at various positions. The pressure-measuring devices 26 can each be of identical configuration or can differ from one another in accordance with the above-described embodiments of the pressure-measuring devices. The closed arrows (not labeled) are merely provided to illustrate how gas can be separated off via the pressure-measuring device during a filling procedure. The treatment system can have one or more disposables and a treatment device. For an understanding of the term disposable and treatment device, reference is made to the comments made further above in the text. The treatment system for extra-corporeal blood treatment can have the following components, the information given below between parentheses showing whether the component is part of a disposable or part of the treatment device, wherein this assignment is to be understood only as optional and not compulsory: A dialyzer 27 (disposable), an arterial line 28 (disposable) with an end connected to an inlet of the dialyzer 27, a venous line 29 (disposable) with an end connected to an outlet of the dialyzer 27, wherein the inlet and the outlet of the dialyzer are fluidically connected to each other, a blood pump 30 (disposable and treatment device) with which blood is pumped in the direction of the dialyzer during the treatment, wherein the blood pump can act on the arterial line. The blood pump 30 can be, for example, a peristaltic pump, wherein the actuator of the pump is part of the treatment device, and a part of the arterial line 28 is designed as a flexible hose element, such that the actuator can act on the latter. Alternatively, the blood pump can also be a diaphragm pump, wherein the diaphragm and the pump vessel are part of the arterial line 28, and the for example hydraulics or pneumatics or mechanics as actuators for moving the diaphragm are part of the treatment device. Alternatively, the blood pump 30 can be an impeller pump, in particular a magnetically driven impeller pump, in which the impeller, as part of the arterial line 28, is arranged in the latter, while the drive for the impeller, in particular the magnetic drive, is designed as part of the treatment device. The following can be provided as further elements: a dialysate feed line 31, which is connected at one end to the dialyzer 27 in order to feed dialysate and/or filling liquid to the dialyzer 27, a dialysate discharge line 32, which is connected at one end to the dialyzer 27 in order to discharge dialysate and/or filling liquid from the dialyzer 27, wherein the dialysate discharge line 32 can be the liquid line 24 as described with reference to FIG. 9, a vessel 33, for example a bag or a canister, which can be connected via a line 34 to the arterial line 28 and/or to the venous line 29, wherein the bag can contain a filling liquid. The dialysate feed line 31 can be connected via a line 36 to the arterial line 28 and/or to the venous line 29. By way of the line 36, substitute liquid can be delivered during the treatment in the case of hemodiafiltration treatment or hemofiltration treatment and/or dialysate or filling liquid can be delivered during the filling operation. The open arrows (not labeled) are merely provided to illustrate how liquid can be transferred, during a filling operation, into the arterial line 28 and/or the venous line 29 and/or the dialyzer 27.

In order to fill a line system which has the arterial line 28, the venous line 29 and the dialyzer 27, the arterial line 28 and the venous line 30, with ends which are connected to the patient during treatment, can be connected to each other directly or can be connected to each other via an adapter. The adapter can be a T-piece or a Y-piece, of which the third opening is connectable to the dialysate discharge line 32. In addition to the discharge via the pressure-measuring device 26, the air can also be able to be discharged via the third opening.

In order to fill a line system which has the arterial line 29, the venous line 30 and the dialyzer 27, an end of the arterial line 29 and an end of the venous line 30, which ends are each connected to the patient during treatment, can be connected individually to the line with the dialysate discharge line 32. For the connections to the line with the dialysate discharge line 32, one or more ports which are fluidically connected to the dialysate discharge line 32 can be provided in the treatment device 25. In addition to the discharge via the pressure-measuring device 26, the air can also be able to be discharged via the one or more ports.

In order to fill a line system which has the arterial line 29, the venous line 30 and the dialyzer 27, an end of the arterial line 29 and an end of the venous line 30, which ends are each connected to the patient during treatment, can be connected individually to the vessel 33. In this embodiment, the blood pump can be controlled to aspirate the liquid from the vessel 33 into the line system. The blood pump can pump the liquid around in a circuit that includes the vessel 33. In addition to the discharge via the pressure-measuring device 26, the air can also be able to be discharged through the semipermeable membrane of the dialyzer 27.

In order to fill a line system which has the arterial line 29, the venous line 30 and the dialyzer 27, an end of the arterial line 29 can be connectable to a connector along the venous line 30, and an end of the venous line 30 can be connectable to the dialysate discharge line 32. For the connection of the venous line 30 to the dialysate discharge line 32, a port which is fluidically connected to the dialysate discharge line 32 can be provided in the treatment device 25. In addition to the discharge via the pressure-measuring device 26, the air can also be able to be discharged via the one or more ports.

In order to fill a line system which has the arterial line 29, the venous line 30 and the dialyzer 27, an end of the arterial line 29 can be connectable to a connector along the venous line 30, and an end of the venous line 30 can be connectable to the vessel 33. In this embodiment, the blood pump can be controlled to aspirate the liquid from the vessel 33 into the venous line 30. The blood pump can pump the liquid around in a circuit that does not include the vessel 33. In addition to the discharge via the pressure-measuring device 26, the air can also be able to be discharged through the semipermeable membrane of the dialyzer 27.

It will be noted at this point that each one of the connections can be usable for the additional discharging of air, for discharging liquid from the line system and optionally for flushing the line system. The treatment system can moreover be programmed in such a way that the connections that are potentially usable for the additional discharging of air can be shut off, for which purpose controllable shut-off elements are accordingly provided. The air can only be discharged via the pressure-measuring device until the liquid wets the hydrophobic membrane and renders the latter impermeable to air. Thereafter, i.e. with the hydrophobic membrane wetted, the pressure-measuring device can be configured to measure the pressure at one point of the line system. In particular, the pressure-measuring device can be configured to measure the pressure in a subsequent blood treatment.

The term "filling the line system" is not to be understood as meaning that the line system has to be completely filled. It is also possible for only partial sections of the line system to be filled by the method described here and using the pressure-measuring device described here.

The pressure-measuring device or the pressure-measuring devices can be arranged between a patient-side end of the arterial line 28 and the blood pump 30 (arterial pressure-measuring device), and/or between the blood pump 30 and the dialyzer 27 (prefilter pressure-measuring device), and/or on the venous line 29, in particular between the dialyzer 27 and an air separation chamber which is arranged on the venous line 29, or on the air separation chamber or with a separate port along the venous line 29 (postfilter pressure-measuring device), and/or on the dialyzer 27.

FIG. 11 shows a schematic view of an embodiment in which the pressure-measuring device is arranged in a cap 42 of the dialyzer 27. The dialyzer 27 has an inlet 38 for blood (during the treatment), an outlet 39 for blood (during the treatment), an inlet 40 for dialysate (during the treatment), and an outlet 41 for dialysate (during the treatment). The region between the inlet for blood and the outlet for blood, which are fluidically connected to each other, (blood chamber) on the one hand, and the region between the inlet for blood and the outlet for dialysate, which are fluidically connected to each other, (dialysate chamber) on the other hand, are separated from each other by a semipermeable membrane. The semipermeable membrane can be in the form of a bundle of hollow fibers. The outlet for the blood is optionally arranged at the top during the filling procedure. This arrangement is known and is used in a wide variety of dialyzer types. At the upper end, the dialyzer 27 can have the cap 42 with an opening 43 and be fluidically connected to the region in which blood is guided during the treatment. The outlet 39 for blood can be arranged in or on the cap 42. Air can escape via this opening 43 during the filling procedure. The pressure-measuring device according to the invention can be provided on or as part of this cap 42. The cap 42 can be dome shaped, and the pressure-measuring device according to the invention can be arranged at the uppermost end of the dome. In this way, air can rise in the dome and be conducted to the pressure-measuring device according to the invention.

Optionally, in the part of the dialyzer 27 opposite the cap 42, the blood pump 30 can be integrated in the dialyzer body, such that the blood pump 30 and a region in which the hollow fibers are arranged form a module. The blood pump 30 can be in particular an impeller pump or can be an impeller of an impeller pump.

A filling method using the blood treatment system can comprise the following steps, which steps do not all have to be implemented:

connecting the line system, which has the arterial line 29, the venous line 30 and the dialyzer 27 and the pressure-measuring device according to the invention, to a source of liquid, filling liquid from a source of filling liquid into the line system, which filling can comprise:

pumping the filling liquid from a dialysate-side chamber through a semipermeable membrane into a blood-side chamber of the dialyzer 27, wherein the pumping is effected by a pump connected to the dialysate feed line 31, and/or aspirating the filling liquid out of the dialysate-side chamber through a semipermeable membrane into a blood-side chamber 27, wherein the aspiration is effected by the blood pump 30, and/or aspirating the liquid out of a vessel 33, wherein the aspiration is effected by the blood pump 30, and/or aspirating the filling liquid from a dialysate-side chamber through a semipermeable membrane into a blood-side chamber of the dialyzer 27 or the vessel 33, wherein the aspiration is effected by a pump connected to the dialysate discharge line 32, and separating the air via the pressure-measuring device during the filling procedure.

The air can be separated via the pressure-measuring device until the hydrophobic membrane is moistened and impermeable to air. An end of the filling procedure can be detected and the pumping can be terminated when the pressure-measuring device detects that the pressure has risen above a predefined limit value. An end of the filling procedure can be detected and the aspiration can be terminated when the pressure-measuring device detects that the pressure has dropped below a predefined limit value.

FIG. 12 shows a schematic view of a further embodiment of the pressure-measuring device. This differs from the other described embodiments in that the first chamber 11 has several channels which are closed off by the hydrophobic membrane 1. The further features correspond to the other features of the described embodiments.

FIG. 13 shows a schematic view of an embodiment of an aeration device. The aeration device differs from the pressure-measuring device described with reference to FIG. 12 in that no pressure sensor 2 is provided. The aeration device can have a closure means 44 for each of the channels of the first chamber 11.

FIG. 14 shows a schematic view of an embodiment of the channels and of the closure means of the aeration device of the aeration device described with reference to FIG. 13. The channels can have flexible regions, for example a hose, which can be closed, in particular pressed closed, by the closure element 44.

FIG. 15 shows a schematic view of an embodiment of the channels and of the closure means of the aeration device of the aeration device described with reference to FIG. 13. The closure means can be a slide, by which the channels can be closed in succession by movement of the slide.

The aeration device, described with reference to FIGS. 11 to 13, can, instead of the pressure-measuring device, be provided on or as part of the cap 42 of a dialyzer, described with reference to FIG. 10. This embodiment is shown schematically in FIG. 16.

In the embodiments of the aeration device described with reference to FIGS. 13 to 16, the hydrophobic membrane 1 covers the plurality of channels. In one embodiment of the aeration device, the hydrophobic membrane 1 can cover the plurality of channels and close each one of the plurality of channels separately, for example with the wall of each individual channel of the plurality of channels being connected at the opening of the channel fixedly and in an airtight and fluid-tight manner, for example by adhesive bonding, welding or crimping. In one embodiment of the aeration device, each of the plurality of channels can be covered with a separate hydrophobic membrane and each one of the plurality of channels can be closed off separately, for example with the wall being connected at the opening of the channel fixedly and in an airtight and fluid-tight manner, for example by adhesive bonding, welding or crimping.

A filling method for a line system, in particular for filling the arterial and/or venous line, can also be a filling method in which either the pressure-measuring device with the hydrophobic membrane is provided or a hydrophobic membrane without pressure-measuring device combined with an impeller pump as blood pump and optionally an aspiration device for aspirating liquid in the direction of the hydrophobic membrane. Since the impeller pump, for example in contrast to a peristaltic pump, cannot pump air, it is necessary, when using an impeller pump, that the liquid can be transferred into the line system in another way than by pumping or aspiration by means of the impeller pump. The hydrophobic membrane may in this case not be a membrane of a dialyzer. The hydrophobic membrane may in this case be a membrane of a dialyzer. The hydrophobic membrane can be arranged on a line section of the line system that is to be filled.

In one embodiment of the filling method, the force of gravity can be used. For this purpose, a source of liquid can be arranged above the line system, and the liquid can fill the line system with the impeller arranged therein.

In a further embodiment, which can be combined with the preceding described embodiment, the filling method can entail generating a pressure gradient across the hydrophobic membrane, for example by means of the aspiration device, which can be part of the dialysate circuit of a dialysis device. In particular, the aspiration device can be arranged on a dialysate discharge line of the dialysis circuit.

During the filling procedure, the air to be displaced can be completely or partially separated via the hydrophobic membrane. If the line system is filled to the extent that the hydrophobic membrane is wetted, no further air can be separated via the hydrophobic membrane.

The dialysis device can have a pressure-measuring device for measuring the pressure in the dialysate discharge line. By means of a control device of the dialysis device, which control device is configured to compare the pressure determined by the further pressure-measuring device with a limit value, a signal for stopping can be transmitted to the aspiration device when the control unit has determined that the pressure is below the limit value.

Alternatively or additionally, a further pressure-measuring device can be provided in the dialysis device for measuring the pressure in the hose portion. By means of a control device of the dialysis device, which control device is configured to compare the pressure determined by the further pressure-measuring device with a limit value, a signal for stopping can be transmitted to the aspiration device when the control unit has determined that the pressure is above the limit value.

Alternatively or in addition, the control device can cause the aspiration device to stop when a predetermined liquid volume has been conveyed by the aspiration device during the filling procedure.

The filling of the line system can be divided into two phases: a first phase, in which the impeller pump is not activated, and a second phase, in which the impeller pump is activated. The first phase can correspond to a phase in which the impeller at least initially is surrounded by air, and the second phase can correspond to a phase in which the impeller is at least partially surrounded by a liquid. In other words, during the filling procedure, the air surrounding the impeller can first be replaced by liquid, and thereafter, when liquid surrounds the impeller and a pumping action by the impeller is thus possible, the impeller pump can be operated and assist the filling procedure.

A change from the first to the second phase can take place in a volume-controlled manner. The control of the dialysis device can be programmed to start a pumping of the impeller pump after a predefined volume has been transferred into the hose set.

Alternatively or in addition, a liquid detection device can be provided on one of the hose lines, in particular downstream from the impeller. The liquid detection device can detect, for example optically or by means of ultrasound or in some other way, that liquid instead of air is present in the hose set, and, since arranged downstream from the impeller, that the impeller must be surrounded by liquid. The control can receive the signal of the liquid detection device and can be programmed to start the pumping of the impeller pump when liquid is detected.

The impeller pump can be a pump in which the impeller is mounted magnetically, i.e., upon activation, the impeller is held suspended in the liquid. Since in this situation the impeller is not in mechanical contact with the surrounding walls, the activation of the pump can also reduce the risk of damage or wear of the impeller.

A corresponding dialysis device can have one, several or all of the following features:
a source of filling liquid, for example a bag or a canister or a connection to a dialysate feed,
a line section of a line system which is connected with a first end to the source of liquid and is connected with a second end to a dialyzer,
an impeller, arranged in the line section,
an impeller drive, for driving the impeller,
a hydrophobic membrane which is arranged along the line section and which separates the interior of the line section from the outside,
an aspiration device which is fluidically connected to the hydrophobic membrane and which is configured to aspirate from the line section via the hydrophobic membrane,
a pressure-measuring device for measuring the pressure in a line between the hydrophobic membrane and the aspiration device,
alternatively or in addition, a further pressure-measuring device for measuring the pressure in the line section,
a control device for starting and stopping the aspiration device and optionally for capturing the measured value of the pressure-measuring device and optionally for starting the impeller drive, wherein the control device can be programmed to stop the aspiration device when the pressure transmitted from the pressure-measuring device drops below a predefined limit value or the pressure transmitted from the further pressure-measuring device rises above a predefined limit value.

The invention claimed is:

1. A pressure-measuring device comprising:
a hydrophobic membrane, which is air permeable in the dry state and air impermeable in a moistened state;
a pressure sensor, which is in mechanical contact with the hydrophobic membrane and which is designed to follow a movement of the membrane;
a first chamber, which is arranged on a front side of the hydrophobic membrane; and
a second chamber, which is arranged on a rear side of the hydrophobic membrane, wherein
the pressure sensor is arranged in the second chamber on the hydrophobic membrane.

2. The pressure-measuring device according to claim 1, wherein the pressure sensor has a pressure-measuring sensor system, and optionally has a carrier layer on which the pressure-measuring sensor system is arranged on the side directed away from the hydrophobic membrane.

3. The pressure-measuring device according to claim 2, wherein the carrier layer has an elastic membrane whose edge region is secured with pretensioning on the first chamber or the second chamber, or wherein the carrier layer is secured on the hydrophobic membrane.

4. The pressure-measuring device according to claim 1, wherein the first chamber, together with the hydrophobic membrane, is secured releasably on the second chamber.

5. The pressure-measuring device according to claim 4, wherein the first chamber, together with the hydrophobic membrane and the pressure sensor, is secured releasably on the second chamber.

6. The pressure-measuring device according to claim 1, wherein the pressure sensor moreover has a cable line in order to transmit an electrical signal to an evaluation unit, wherein the cable line optionally has a connector unit for connecting and/or releasing the pressure sensor with respect to the evaluation unit.

7. The pressure-measuring device according to claim 1, wherein the first chamber has at least two channels, which are each closed off at one end by the hydrophobic membrane.

8. The pressure-measuring device according to claim 7, wherein at least two of the at least two channels can be shut off individually.

9. A method for measuring a pressure using a pressure-measuring device according to claim 8, comprising:

filling a blood hose system with a liquid by displacement of air in the blood hose system through the hydrophobic membrane, wherein the hydrophobic membrane is wetted by the liquid such that it becomes impermeable to air in the region of one of the at least two channels, and measuring the change of the position of the membrane by the pressure sensor.

10. A method for measuring a pressure using a pressure-measuring device according to claim 7, comprising:

filling a blood hose system with a liquid by displacement of air in the blood hose system through the hydrophobic membrane, wherein the hydrophobic membrane is wetted by the liquid such that it becomes impermeable to air or becomes impermeable to air in the region of one of the at least two channels, and measuring the change of the position of the membrane with respect to its shape, by the pressure sensor.

11. A medical functional device having at least one blood line and/or a dialyzer, for use with a pressure-measuring device according to claim 1, wherein the first chamber and the hydrophobic membrane, or wherein the first chamber and the hydrophobic membrane and the pressure sensor, are part of the medical functional device.

12. The medical functional device according to claim 11, having a line section which is designed for insertion into a peristaltic pump, or having an impeller pump or having a diaphragm pump, wherein the pressure-measuring device is arranged fluidically upstream or downstream from the pump, and/or having an air separation chamber, wherein the pressure-measuring device is arranged fluidically upstream or downstream from the air separation chamber, and/or having a dialyzer, wherein the pressure-measuring device is arranged on the dialyzer.

13. The pressure-measuring device according to claim 1, wherein the pressure sensor has a pressure-measuring sensor system that is a strain gauge sensor system or a piezoelectric sensor.

14. The pressure-measuring device according to claim 1, wherein the pressure sensor has a pressure-measuring sensor system that is a strain gauge sensor system or a piezoelectric sensor and has a carrier layer on which the pressure-measuring sensor system is arranged on the side directed away from the hydrophobic membrane.

15. A method for measuring a pressure using a pressure-measuring device according to claim 1, comprising:

filling a blood hose system with a liquid by displacement of air in the blood hose system through the hydrophobic membrane, wherein the hydrophobic membrane is wetted by the liquid such that it becomes impermeable to air, and measuring the change of the position of the membrane by the pressure sensor.

\*  \*  \*  \*  \*